(12) United States Patent
Zavislan et al.

(10) Patent No.: US 6,745,067 B1
(45) Date of Patent: Jun. 1, 2004

(54) SYSTEM FOR MARKING THE LOCATIONS OF IMAGED TISSUE WITH RESPECT TO THE SURFACE OF THE TISSUE

(75) Inventors: James M. Zavislan, Pittsford, NY (US); Roger J. Greenwald, San Diego, CA (US)

(73) Assignee: Lucid, Inc., Rochester, NY (US)

( * ) Notice: Subject to any disclaimer, the term of this patent is extended or adjusted under 35 U.S.C. 154(b) by 0 days.

(21) Appl. No.: 09/786,902

(22) PCT Filed: Sep. 13, 1999

(86) PCT No.: PCT/US99/21116

§ 371 (c)(1),
(2), (4) Date: Mar. 9, 2001

(87) PCT Pub. No.: WO00/15105

PCT Pub. Date: Mar. 23, 2000

Related U.S. Application Data

(60) Provisional application No. 60/100,176, filed on Sep. 14, 1998.

(51) Int. Cl.[7] .................................................. A61B 6/00
(52) U.S. Cl. ...................................... 600/473; 600/476
(58) Field of Search .............................. 600/407, 473, 600/476; 359/368, 396, 397; 382/128; 356/244

(56) References Cited

U.S. PATENT DOCUMENTS

| 5,020,088 A | | 5/1991 | Tobin |
| 5,034,613 A | | 7/1991 | Denk et al. |
| 5,108,926 A | | 4/1992 | Klebe |
| 5,146,923 A | * | 9/1992 | Dhawan |
| 5,428,690 A | | 6/1995 | Bacus et al. |
| 5,532,874 A | * | 7/1996 | Stein .......................... 359/394 |
| 5,719,700 A | | 2/1998 | Corcuff et al. |
| 5,740,270 A | | 4/1998 | Rutenberg et al. |
| 5,788,639 A | | 8/1998 | Zavislan et al. |
| 5,791,346 A | | 8/1998 | Craine et al. |
| 5,836,877 A | | 11/1998 | Zavislan |
| 5,880,880 A | | 3/1999 | Anderson et al. |
| 5,978,695 A | | 11/1999 | Greenwald et al. |
| 5,995,283 A | | 11/1999 | Anderson et al. |
| 5,995,867 A | | 11/1999 | Zavislan et al. |
| 6,032,071 A | * | 2/2000 | Binder ....................... 600/476 |
| 6,151,127 A | | 11/2000 | Kempe |
| 6,424,852 B1 | * | 7/2002 | Zavislan ..................... 600/407 |

FOREIGN PATENT DOCUMENTS

WO          WO 98/17166        4/1998

OTHER PUBLICATIONS

Corcuff, P. et al., Morphometry of Human Epidermis in vivo by Real–time Confocal Microscopy, Arch Dermatol Res, 265, pp. 475–481, 1993.
Rajadhyaksha, M. et al., Confocal Laser Microscope Images Tissue In vivo, Laser Focus World, pp. 1–4, Feb. 1997.
Schmitt, J. et al., Optical Characterization of Dense Tissues Using Low–Coherence Interferometry, SPIE, vol. 1889, pp. 197–211, 1993.

* cited by examiner

*Primary Examiner*—Shawna J. Shaw
(74) *Attorney, Agent, or Firm*—Kenneth J. Lukacher

(57) ABSTRACT

A system is provided for marking on a recording medium (36), such as a label, the location of imaged tissue with respect to an exposed surface of the tissue (34). Tissue is imaged by a microscope (11) capable of imaging sections of the tissue below the exposed tissue surface through optics. A ring (32) applied to the surface of the tissue stabilizes the tissue to the optics and localizes a portion of the tissue surface through an aperture in the ring. An actuator (38) is connected to both the ring and the microscope for moving the ring to adjust the position of the tissue with respect to the optics, thereby allowing an operator of the system to survey different images of tissue sections with the microscope.

58 Claims, 7 Drawing Sheets

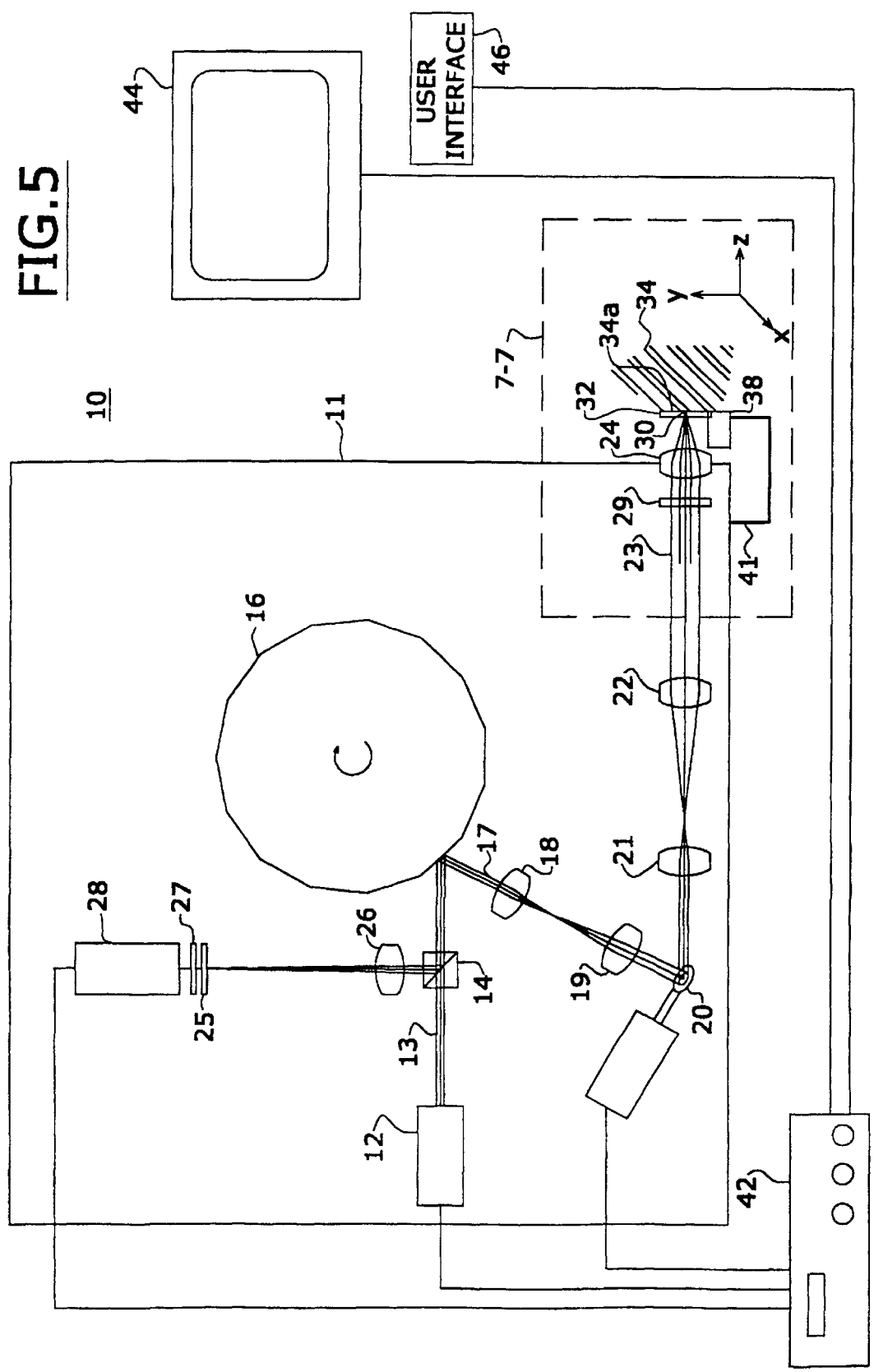

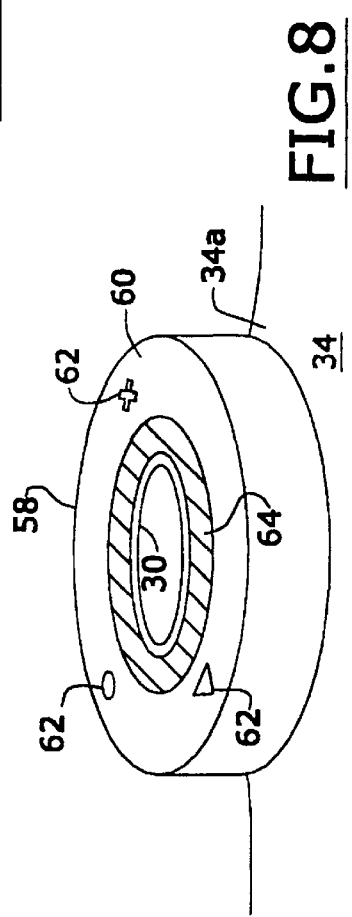
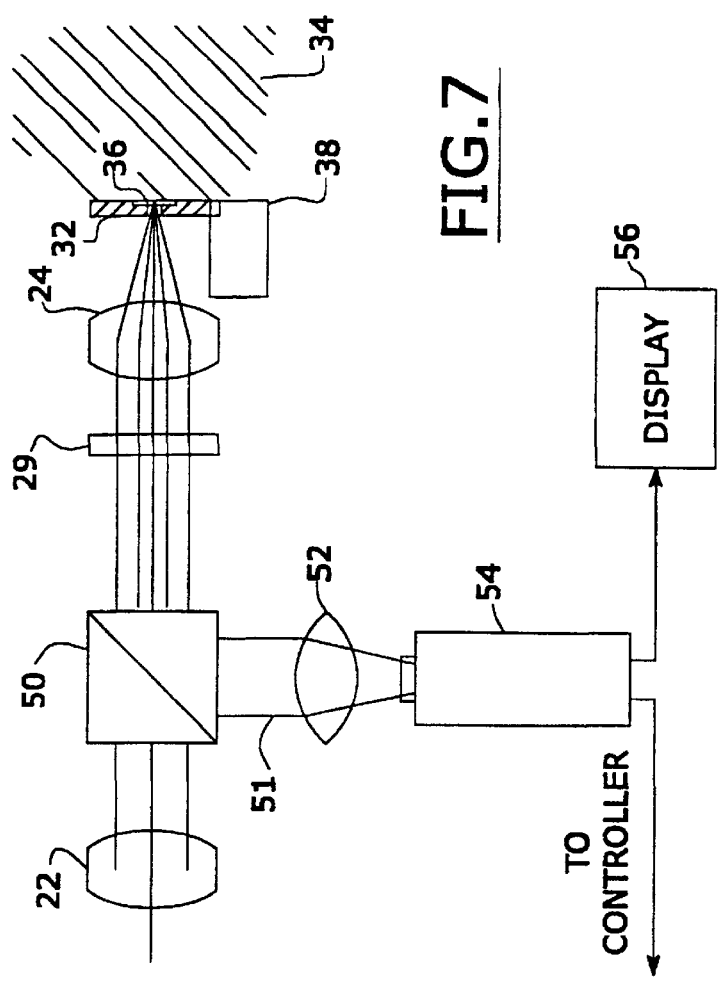
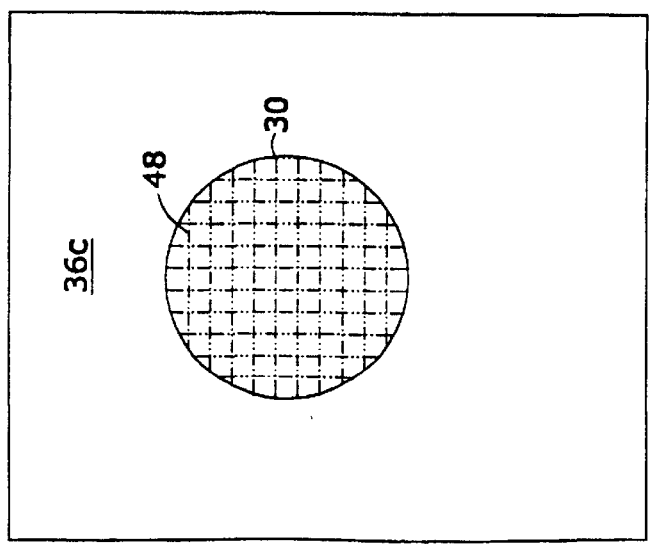

SYSTEM FOR MARKING THE LOCATIONS OF IMAGED TISSUE WITH RESPECT TO THE SURFACE OF THE TISSUE

This application claims the benefit of priority to U.S. Provisional Patent Application Serial No. 60/100,176, filed Sep. 14, 1998 now abandoned.

DESCRIPTION

FIELD OF THE INVENTION

The present invention relates to a system for marking on a recording medium, such as a label, the locations of imaged tissue with respect to the surface of the tissue, and relates particularly to, a system for marking on a recording medium the locations of tissue sections imaged by a microscope, such as a confocal microscope, which is of pathological interest. Such marks are useful for directing treatment of the tissue.

BACKGROUND OF THE INVENTION

Confocal microscopy involves scanning tissue to produce microscopic sectional images of surface or subsurface tissue. Such microscopic imaged sections may be made in-vivo and can image tissue at cellular resolutions. Examples of confocal scanning microscopes are found in U.S. Pat. Nos. 5,788,639 and 5,880,880, and in articles by Milind Rajadhyaksha et al., "In vivo Confocal Scanning Laser Microscopy of Human Skin: Melanin provides strong contrast," The Journal of Investigative Dermatology, Volume 104, No. 6. June 1995, pages 1–7, and by Milind Rajadhyaksha et al., "Confocal laser microscope images tissue in vivo," Laser Focus World, February 1997, pages 119–127. These systems have confocal optics which direct light to the patient's tissue and image tissue sections from the returned reflected light. These confocal systems, although useful for microscopic examination of a tissue lesion or other abnormal tissue, have no capability for identifying locations on the surface of the tissue where the imaged lesion is within the tissue. Without such identification, the physician does not know after imaging the particular locations in the imaged tissue to carry out treatment of the lesion viewed in the images. Such treatment may include excising the tissue from the patient, radiation therapy, or ablation. Since treatment can harm healthy tissue which may lie near a lesion, precise location of the lesion is of importance. Also, without the capability to identify on the tissue surface the locations of an imaged lesion, it may be difficult for a physician to locate the lesion in future examinations for observing possible changes in the condition of the tissue when treatment of the lesion is deferred or is non-invasive.

SUMMARY OF THE INVENTION

Accordingly, the principal feature of the present invention is to provide an improved system for marking on a recording medium, such as the label, the locations of imaged tissue sections with respect to the surface of the tissue, in which such tissue section may present a lesion or other abnormal parts of the tissue.

Another feature of the present invention is to provide an improved system for providing macroscopic markings of the location of one or more selected microscopic sectional images of tissue with respect to the surface of such tissue.

A further feature of the present invention is to provide an improved system for automatically or manually marking the location of one or more microscopic sectional images of tissue with respect to the surface of such tissue.

Briefly described, the present invention embodies a system including a microscope having optics through which the microscope can image tissue sections below the surface of the tissue. A tissue stabilization mechanism is provided by a ring applied to the surface to the tissue for stabilizing the tissue and localizing a portion of the surface of the tissue through an aperture in the ring. Connected to both the ring and the microscope is an actuator which moves the ring to adjust the position of the tissue with respect to the optics. This actuator allows an operator of the system to survey different images of tissue sections with the microscope. A programmed controller is provided to enable the operator to select one or more imaged tissue sections to be marked, and for obtaining location information representing the location in the tissue of each selected tissue section with respect to the surface of the tissue. After imaging, the microscope is detached from the actuator and marks are produced on the recording medium in accordance with the location information either automatically by a print head located in the ring and operated by the controller, or manually by an operator applying such marks with a pen. Marks manually made on the recording medium may be based on the location information provided to the operator by the controller, such as via a display coupled to the controller. A single mark may reference one or more selected tissue sections. These marks indicate the location on the tissue surface of the sub-surface tissue presented in each of the selected tissue sections.

In a first embodiment of the system, the recording medium is located between the surface of the tissue and the aperture of the ring, and the controller determines the location information for each selected image with respect to indicia on the recording medium representing an origin for the location information.

In a second embodiment of the system, the recording medium is also located between the surface of the tissue and the aperture of the ring, and the controller determines the location information with respect to indicia on the recording medium corresponding to different locations on the surface of the tissue. Such indicia may have lines of symbols encoding different locations of the tissue surface, which may be read and decoded by the controller to determine the location information of each selected tissue section.

In a third embodiment of the system, the ring has a template with holes for placing reference marks on the surface of the tissue around the tissue in the aperture of the ring. The controller determines the location information of selected tissue sections in reference to the location of the holes in the template. The recording medium in this embodiment is the surface of the tissue, such that after imaging either the template holes are used by a printer head placed in the ring to produce marks on the tissue in accordance with the location information, or the ring is removed and the reference marks are used by an operator to apply marks on the surface of the tissue in accordance with the location information.

In a fourth embodiment of the system, the recording medium is located on a platen that is coupled to the ring to be movable therewith, and the system includes a pen coupled to the microscope which is positioned over the recording medium. When each tissue section is selected by the operator, the pen applies a mark on the recording medium. This both determines the location information and produces marks on the recording medium indicating the location on the surface of the tissue of each selected tissue section. After imaging and detachment of the microscope from the actuator, the recording medium may be placed on the surface of the tissue in the aperture of the ring.

Marks on the recording medium identify the location of the tissue in selected tissue sections below the tissue surface for subsequent viewing or treatment. The microscope in the above embodiments is preferably a confocal microscope which provides images of tissue sections below the tissue surface. However, other microscopes may be used to provide images of the tissue, such as microscopes employing optical coherence tomography, or two-photon microscopy.

Further, the term tissue as used herein generically refers to any natural or surgically exposed surface of the body of the patent, such as skin, teeth, oral mucosa, cervix, or internal body-tissue during surgery. Tissue may also represent a tissue specimen removed from a patient.

BRIEF DESCRIPTION OF THE DRAWINGS

The foregoing features and advantages of the invention will become more apparent from a reading of the following description in connection with the accompanying drawings, in which:

FIG. 5 is a block diagram of the system in accordance with a second embodiment of the present invention showing a microscope for imaging tissue through a tissue stabilization mechanism;

FIG. 6 illustrates an example of the recording medium located between the surface of the tissue and the tissue stabilization mechanism of FIG. 5 in which the medium has indicia encoding location information;

FIG. 7 is an enlarged block diagram of the part of the system of FIG. 5 shown within the box enclosed by dashed line 7—7 in FIG. 5 which includes an optional video camera for visualizing the recording medium;

FIG. 8 is perspective view of a tissue stabilization mechanism in accordance with a third embodiment of the present invention having a ring with a template for establishing reference marks on the surface of the tissue;

DETAILED DESCRIPTION OF THE INVENTION

Figure 1:
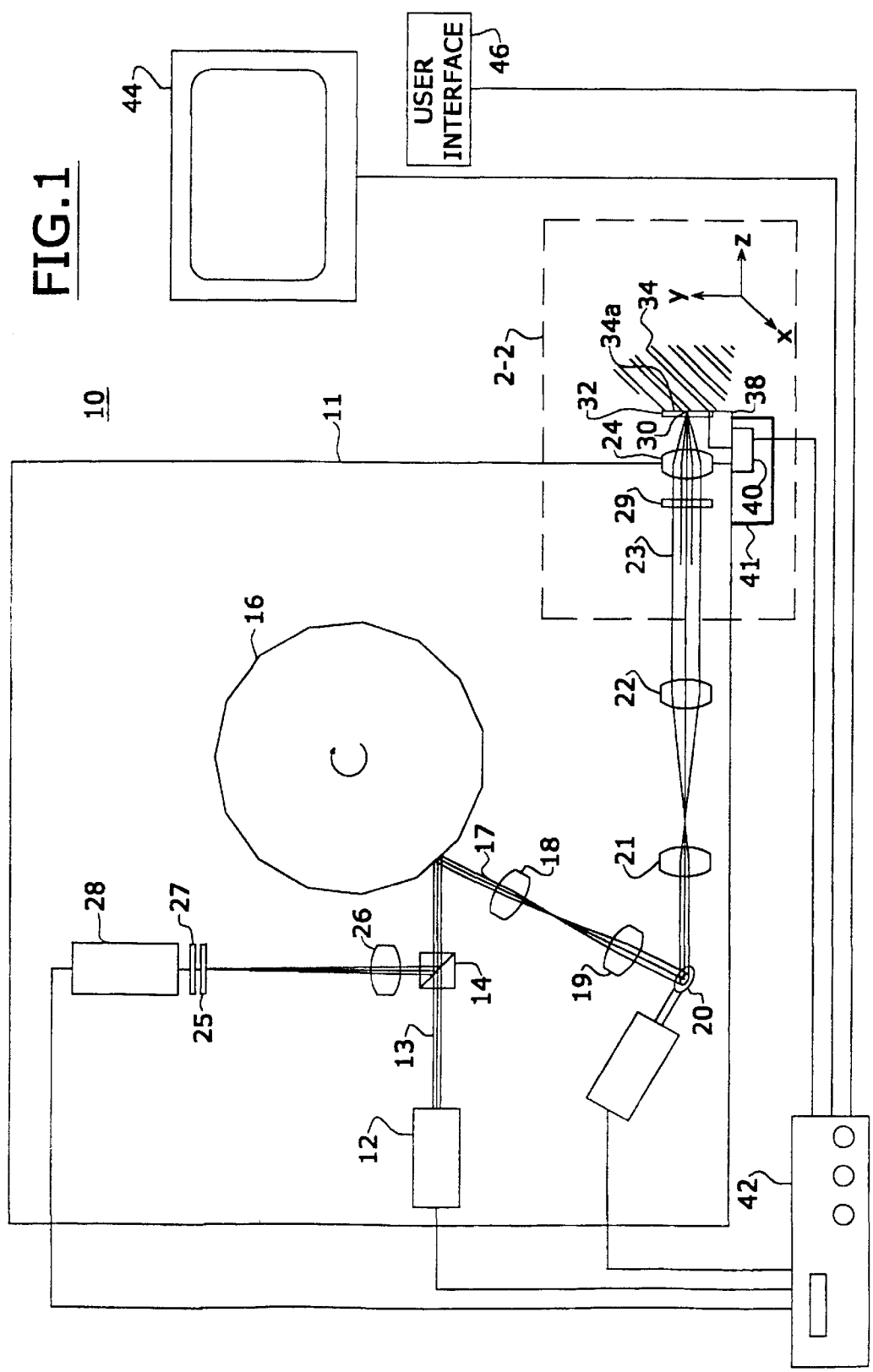
FIG. 1 is a block diagram of a system in accordance with a first embodiment of the present invention showing a microscope for imaging tissue through a tissue stabilization mechanism.
Figure 2B:
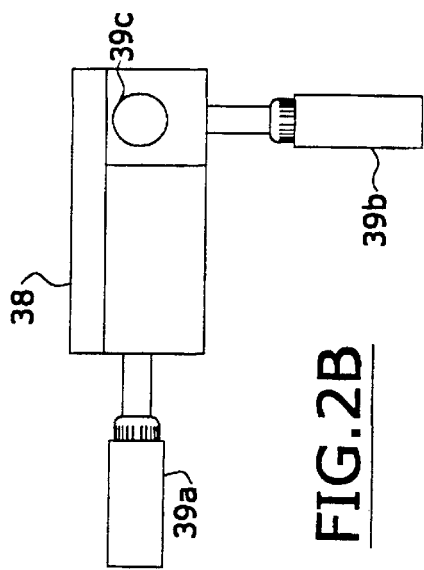
FIG. 2B is a side view of the mechanical actuator in the system of FIGS. 1 and 2.
Figure 2:
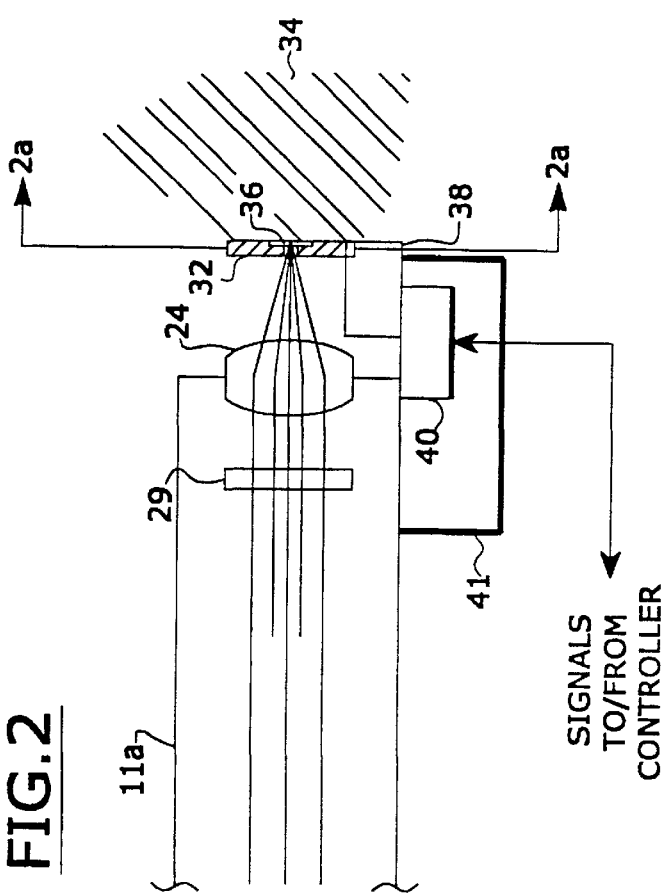
FIG. 2 is an enlarged block diagram of the part of the system of FIG. 1 shown within the box enclosed by dashed line 2—2 in FIG. 1.

Referring to FIGS. 1 and 2, a system 10 includes a confocal microscope 11 having a laser 12 for producing light (a laser beam) at an infrared wavelength along a path 13 through beam-splitter 14 onto a rotating polygon mirror 16. Polygon mirror 16 has a plurality of mirror facets to reflect the beam from laser 12 at varying angles responsive to the rotation of mirror 16, i.e., to repeatedly scan the beam. The reflected beam from rotating polygon mirror 16 travels along a path 17 through relay and focusing lenses 18 and 19 onto a galvanometer mirror 20. Lenses 18 and 19 image the beam reflected by the polygon mirror facet onto galvanometer mirror 20. Galvanometer mirror 20 reflects the beam incident thereto at a controlled angle through lenses 21 and 22 along a path 23 to an objective focusing lens 24. Lenses 21 and 22 image the beam reflected by galvanometer mirror 20 onto objective lens 24. A quarter-wave plate 29 is provided in path 23 between lens 22 and objective lens 24. Objective lens 24 is preferably in a fixed position in confocal microscope 11.

The beam through objective lens 24 is then focused to a tissue 34 through a mechanism which stabilizes tissue 34 to lens 24 for minimizing undesirable motion of the tissue. This mechanism includes a ring or annulus 32 (shown in cross-section in FIG. 1) having an aperture 30 for localizing an area of the tissue to objective lens 24. An adhesive layer between the surface 34a of tissue 34 and the surface of ring 32 facing surface 34a bonds ring 32 to the tissue.

Figure 2A:
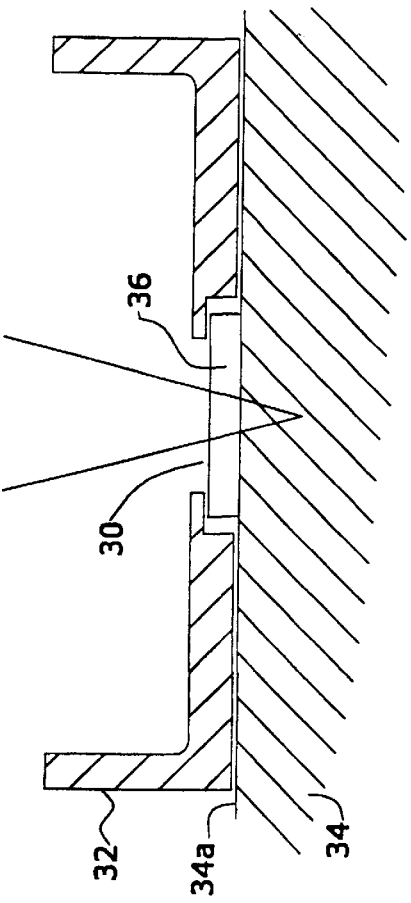
FIG. 2A is a cross-section of the tissue stabilization mechanism of FIGS. 1 and 2 in the direction of the arrows 2a—2a in FIG. 2.

As best shown in FIGS. 2 and 2A, a recording medium 36 is located under aperture 30 on the surface 34a of the tissue. Medium 36 is transparent to the laser radiation and may be a label made of thin non-elastic material, such as polyurethane or amphorous polyolefin. Medium 36 has an adhesive layer on its surface facing, tissue 34 for positioning the label on tissue surface 34a Alternatively, medium 36 may a thin glass plate situated in a recess in the ring 32 between aperture 30 and the tissue surface 34a Medium 36 has indicia viewable through aperture 30. These indicia will be described later in connection with FIGS. 3A and 3B. Optionally, an index matching fluid, such as saline or mineral oil, may be present between medium 36 and the surface 34a below aperture 30 to reduce undesired surface reflection of the laser beam.

The beam from lenses 21 and 22 is focused by objective lens 24 through aperture of ring 32 at a spot within tissue 34, or on its surface 34a or at medium 36. The returned reflected light from tissue 34 is collected by objective lens 24. The reflected light travels from objective lens 24 through lenses 22 and 21 to galvanometer mirror 20. Mirror 20 reflects the light to rotating polygon mirror 16 via lenses 19 and 18, and then polygon mirror 16 reflects the light onto beam-splitter 14. Beam-splitter 14 reflects the light through lens 26 onto a detector 28, via a confocal pinhole 27 to produce a confocal image on detector 28. Detector 28 may be a solid-state detector, such as an avalanche photodiode. An optional shutter 25 may be provided in the path of the light to detector 28, if needed to selectively block or filter light to the detector. Except for ring 32, the above described components provide the confocal imaging microscope 11 in system 10 which may be situated at a station or within a portable microscope head. As shown in FIG. 2, microscope 11 may have a projecting member 11a containing at least the objective lens 24 of the optics of the microscope.

System 10 also includes a mechanical actuator 38, such as a translation stage, connected to ring 32 for moving the ring in three approximately orthogonal directions x, y, and z, where the plane formed by the x and y axes is substantially parallel with the tissue surface 34a and the z axis is substantially parallel to the optical axis of objective lens 24. Actuator 38 is attached to microscope 11 by a coupler 41, such that the actuator moves ring 32 while lens 24 is fixed with respect to the actuator. Ring 32 may be coupled to actuator 38 by means of magnetic coupling, friction interface screw, or mechanical latching. Coupler 41 represents any means for attaching actuator 38 to microscope 11. Coupler 41 may also allow the microscope 11 to be detached therefrom. As shown in FIG. 2B, a set of three micrometers 39a, 39b, 39c in actuator 38 serves to move ring 32 manually. Each micrometer is capable of moving ring 32 in a different orthogonal direction x, y, or z. These micrometers thus control the position of ring 32 with respect to objective lens 24. These micrometers may be similar to micrometers on a conventional microscope stage. Alternatively, actuator 38 may move lens 24 instead of ring 32 in the three orthogonal directions, while ring 32 remains fixed to microscope 11.

In microscope 11, preferably the imaging laser beam is linearly polarized, and beam-splitter 14 is a polarizing beam-splitter. Quarter-wave plate 29 is located in path 23 between lenses 22 and 24 for converting specularly reflected light from the tissue to a polarization state orthogonal to the incident illumination of the laser beam to the tissue; this orthogonally polarized light is reflected by beam-splitter 14 to detector 28. The rotating polygon mirror 16 and galvanometer mirror 20 provide a scanning mechanism in system 10 for scanning the beam of laser 12 in two of the three orthogonal directions through a plane in the tissue. These orthogonal directions may be generally parallel with the x, y, and z axes of actuator 38. However, other scanning mechanisms may be used, such as two galvanometer mirrors which direct the beam of laser 12 along paths 17 and 23, respectively, holographic or diffractive scanning, or transverse mechanical scanning of objective lens 24.

System 10 further includes a programmed controller 42, such as a personal computer, for controlling the operation of the system. Controller 42 can enable laser 12 and control the laser's operating parameters, such as the energy density (or intensity), pulse width, power, duty cycle, and wavelength, of the beam emitted from laser 12. Controller 42 may also control the operating (or beam delivery) parameters of the confocal optics, such as the scan rate of the scanning mechanism, setting of shutter 25, and area of illumination (scan width and height), i.e., the field of view of the confocal optics. The scanning mechanism is controlled by controller 42 by enabling the rotation of polygon mirror 16 via a motor (not shown), and the angular position of galvanometer mirror 20. The depth of focus in the tissue of the laser beam is determined by the position of ring 32 by actuator 38 along the z direction.

Controller 42 also receives electrical signals from a position encoder 40 of actuator 38 representing the present x, y, and z coordinates of the micrometers of actuator 38. For example, such signals may represent three binary coded decimal numbers. The position encoder may have three up/down digital counters containing the value of the x, y and z coordinates, respectively. Each counter indexes up one when their respective x, y, z micrometer moves a preset distance in a positive direction, and indexes down one when their respective micrometer moves the same preset distance in the opposite or negative direction. The x, y, z coordinates may also provide negative or positive values depending on the direction the micrometers are moved by the operator.

Thus, controller 42 monitors the position of the micrometers of actuator 38 by position encoder 40. Other means for encoding the position of the micrometers may also be used which are similar to monitoring the position of a translation stage of conventional microscopes. Electrical signals can also be sent by controller 42 to actuator 38 for resetting the x, y, z coordinates of its micrometers to zero, i.e., resetting the value of the counters to zero, thereby establishing an origin for the coordinate system of the micrometers of actuator 38.

Detector 28 provides controller 42 signals representing confocal images. As the scanning mechanism scans the tissue, successive frames of confocal images are provided in real-time to controller 42 from detector 28. The controller 42 drives a display 44 to display as a raster scan the confocal images. The displayed confocal image is a two-dimensional digital image composed of a two-dimensional pixel array.

Microscope 11 operates in system 10 by projecting the beam from laser 12 through the confocal optics into tissue 34 while the scanning mechanism scans the projected beam along a microscopic image plane below tissue surface 34a through aperture 30. A microscopic tissue section is produced on display 44 based on the return collected light from the image plane. The location of the microscopic image plane in the tissue is determined by the position of tissue 34 in aperture 30 with respect to the projected beam (and lens 24), as set by actuator 38. The orientation of the image plane, either vertical or horizontal, is determined by the two orthogonal directions of the scanning mechanism. For example, scanning in the x and y directions, which is generally parallel to the x and y axis of actuator 38, provides a horizontal image plane and a horizontal tissue section on display 44. Scanning in the x and z directions, which is generally parallel to the x and z axis of actuator 38, provides a vertical image plane and a vertical tissue section on display 44.

Figure 3B:
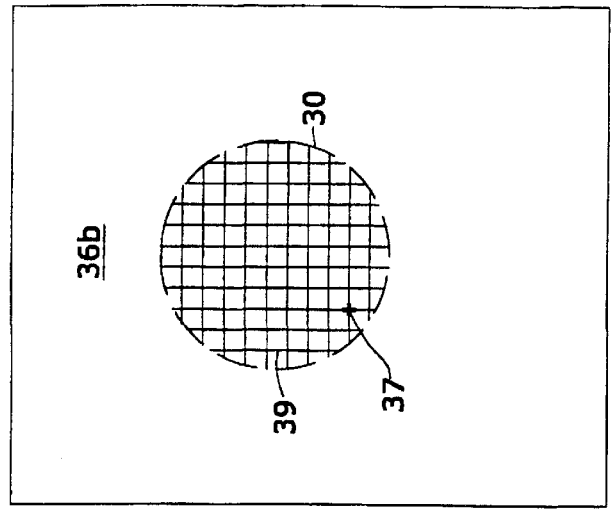
FIGS. 3A and 3B illustrate two examples of recording medium between the surface of the tissue and the tissue stabilization mechanism of FIG. 1 in which the medium has indicia referencing an origin location.
Figure 3A:
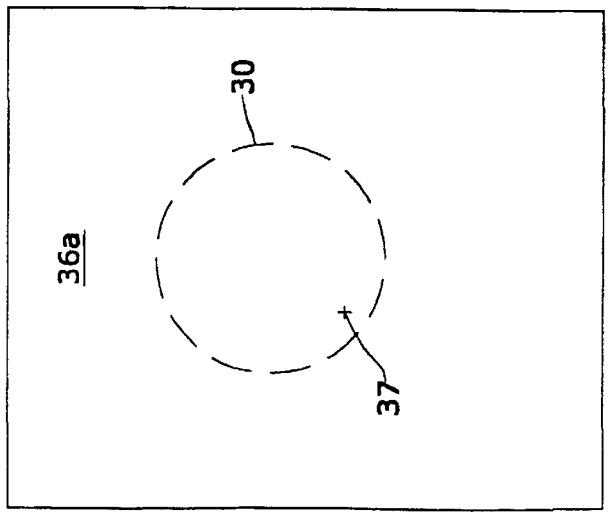

Referring to FIGS. 3A and 3B, examples of two types of recording medium 36, label 36a and label 36b are shown. (Aperture 30 is shown in dashed lines in FIGS. 3A and 3B.) The only difference between labels 36a and 36b is that label 36b has indicia of a printed grid 39, and label 36a does not. However to microscope 11, labels 36a and 36b appear the same since the ink used in the lines of grid 39 is composed of a leuco dye which is transparent to infrared wavelength light produced by laser source 12. Label 36a and 36b each have indicia representing a zero reference mark 37. The cross-hairs of zero reference mark 37 are aligned parallel with the x and y axes of actuator 38, i.e., the axes of the x and y micrometers which move ring 32 in x and y directions. Raised ridges in medium 36 may be received in grooves in ring 32 to align mark 37 parallel to these x and y axes. Mark 37 is printed with ink on labels 36a and 36b which is visible to microscope 11. Although mark 37 is illustrated as a cross-hair, it may be any mark having which provides a shape alignable with the x and y axes of actuator 38, and is of a sufficient size to be focusable by microscope 11.

A user interface 46, such as a mouse, keyboard, light pen, or the like, allows an operator to input to controller 42 commands for operating system 10. These commands include resetting the origin of x, y, z coordinate of the micrometers in actuator 38, and selecting an imaged tissue section presenting the part of the tissue 34 to be marked. In response to each selected tissue section, controller 42 stores the x, y, z coordinates received from position encoder 40 into a database in its memory. During imaging, coordinates received from position encoder 40 may be displayed by controller 42 on display 44 to assist the operator in selecting tissue sections to be marked. Although, the micrometers of actuator 38 are preferably manually operated, the micrometers may be operated by controller 42 in which the operator controls their movement via commands entered on interface 46, which may have a typical joystick for controlling three directional motion.

Figure 4:
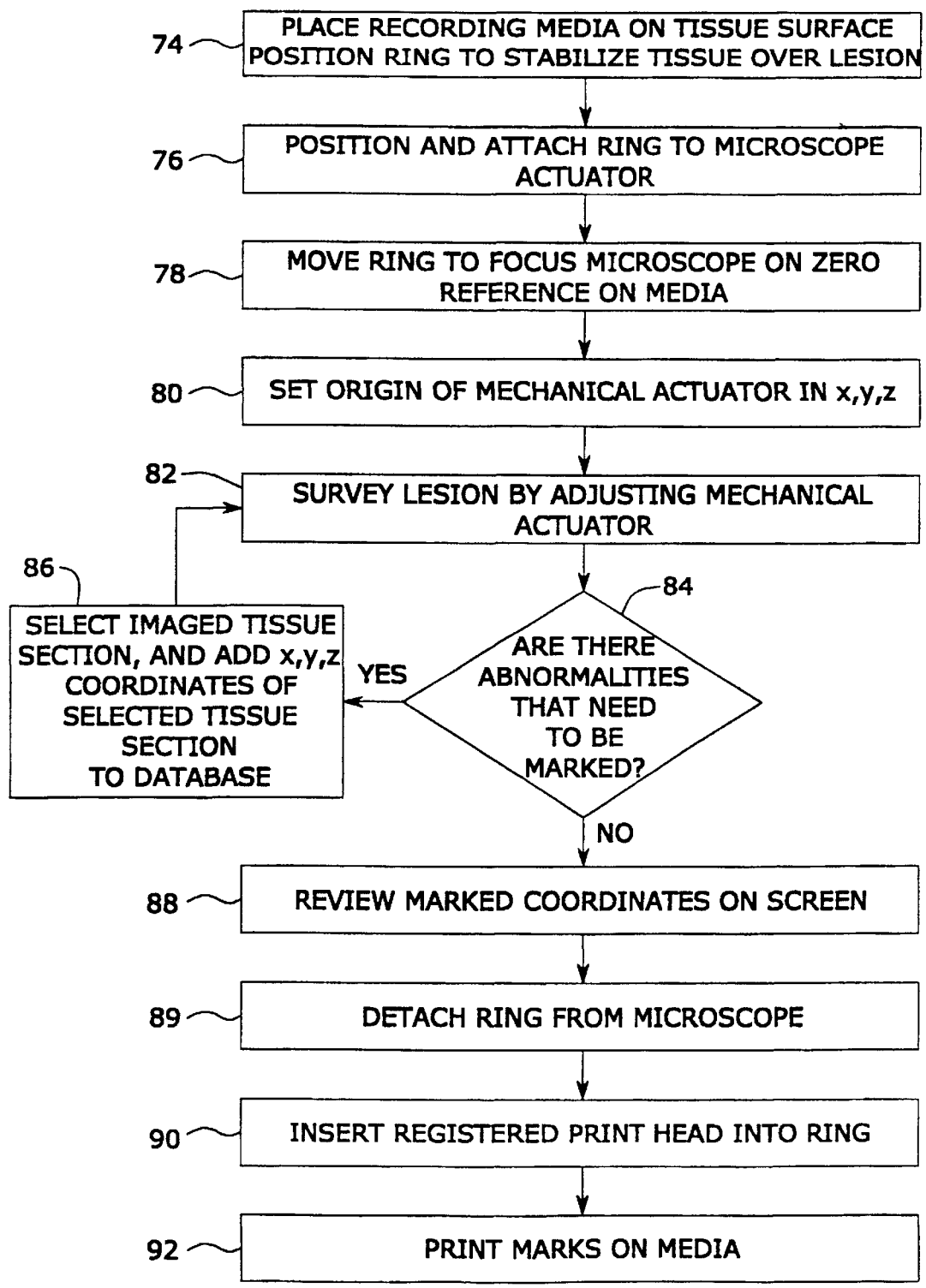
FIG. 4 is a flow chart of a sequence of operation of the system of FIG. 1 which includes automatic marking.

Referring to FIG. 4, the operation of system 10 will now be described. Prior to imaging of the tissue, the operator applies recording medium 36 onto the surface of the tissue to be imaged (step 74). The adhesive layer on medium 36 holds it onto tissue surface 34a Further, at step 74 the tissue stabilization mechanism of ring 32 is then positioned on tissue 34 over medium 36, such that aperture 30 is positioned to localize the volume of tissue 34 having the tissue to be imaged, and mark 37 appears in the aperture in alignment parallel to the x and y axes of actuator 38. Actuator 38 and rinse 32 provide a single assembly when ring 32 is positioned onto tissue 34. Ring 32 bonds to the surface 34a of the tissue by an adhesive layer between ring 32 and the tissue 34.

Next, the operator positions microscope 11 such that its objective lens 24 is placed over ring 32, and then attaches actuator 38 to the microscope via coupler 41 (step 76). This stabilizes the portion of the tissue in aperture 30 to the optics of microscope 11. The microscope provides controller 42 signals from detector 28 representing images of the tissue, and displays the images on display 46. With the scanning mechanism of microscope 11 scanning the beam focused by lens 24 generally along a horizontal plane parallel to the x and y axes of actuator 38, the operator adjusts the x, y, and z micrometers of actuator 38 to move ring 32 such that the zero reference mark 37 on medium 36 is in focused in the center of the image on display 44 (step 78). The operator, via interface 46, then directs controller 42 to set the origin for the x, y, z coordinate system of actuator 38. In response, controller 42 sends a signal to actuator 38 to reset the x, y, z coordinates associated with its micrometers to zero (step 80).

With the origin established, the operator surveys the portion of tissue 34 under aperture 30 by adjusting the micrometers and viewing the images of the tissue sections on display 44 (step 82). Such images may represent horizontal or vertical sections through the tissue, depending on the scanning direction of the scanning mechanism of microscope 11, as described earlier. Scanning direction of the scanning mechanism may be selected by the operator via interface 46. These images are of cellular resolution of the surface or subsurface cells of the tissue. While surveying the tissue, the operator examines the imaged tissue (or cells) in the tissue section on display 44 for abnormalities associated with a lesion in the tissue, or for other tissue structures desired to be marked (step 84). For example, the operator may survey the tissue for images showing the margins of the lesion which define the boundary between the tissue of the lesion and healthy tissue. If abnormalities are presented in the tissue section on display 44, the operator directs controller 42, via interface 46, to select that imaged tissue section for later marking of its location in the tissue 34 (step 86). Optionally, before the operator directs controller 42 to A select the imaged tissue section, the operator may center the abnormal tissue on the display using the micrometers of actuator 32. In response, controller 42 reads the signals from the position encoder 40 of actuator 38 representing the x, y, z coordinates of the micrometers of actuator 38, and stores the coordinates in the database allocated in the memory of controller 42. These x, y, z coordinates represent location information which correlates the location of the tissue section on display 44, within the volume of tissue below tissue surface 34a in reference to the established origin. Specifically, the x, y coordinates from position encoder 40 represent the location on the surface of the tissue of the selected image, while the z coordinate represents the depth of the selected image from the surface.

The surveying and selecting of imaged tissue sections to be marked is repeated (steps 82, 84 and 86) until no more imaged tissue having abnormalities are found, or the operator determines that the margins of the lesion are adequately represented by the selected tissue sections. The operator then reviews the coordinates of the selected tissue sections stored in the database on display 44 (step 88). For example, controller 42 may represent the x, y, z coordinates of the selected tissue sections on display 44 as a three-dimensional image, or may represent only the x, y coordinates of each selected tissue section as a two-dimensional image on display 44.

Figure 3C:
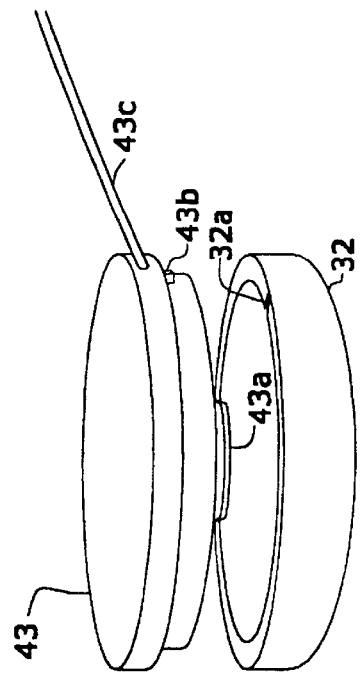
FIG. 3C is an example of a printing mechanism locatable in the tissue stabilization mechanism of FIGS. 1 and 2.

After imaging with microscope 11, actuator 38 is detached from the microscope (step 89). Marks are produced on medium 36 based on the x, y, z coordinates of the selected tissue sections in the database either automatically with a print head (step 90), or manually by the operator. For automatic marking, a print head is situated in ring 32 having an array of print elements which lie in registration in ring 32, and in alignment with both the zero reference mark and the x and y axes of actuator 38. An example of the print head 43 is shown in FIG. 3C, including printing elements 43a which can be located in aperture 30 of ring 32 against recording medium 36, such that a registration slot 32a of ring 32 receives a tab 43b of printhead 43 in order to align the printhead, i.e., associate the position of printing elements with the x, y coordinates of the x and y axes of actuator 38. Controller 42 sends signals to the print head to instruct it's printing elements to place marks on medium 36 based on the x, y coordinates of each selected tissue section in the database (step 92), such as via a data cable 43c between controller 42 and printhead 43. The z coordinate, which represents the relative tissue depth of each selected tissue section, may be represented by different color or density ink on the medium. Marks may appear as dots or crosses, or any other shape visible to the operator without the need for a conventional optical microscope. The operator may instruct the controller to connect all or some of the marks, such as to outline the margins of a lesion in the tissue.

Further, the automatic marking of step 90 may also be done by a pen attached to coupler 41 such that the length of the pen is aligned with the former location of the optical axis of lens 24. The micrometers of actuator 38 are then automatically operated by controller 42 to move the tissue (or pen) until the x, y coordinates of position encoder 40 of actuator 38 equals the x, y coordinates of a selected tissue section. The pen either automatically or manually applies a mark on medium 36 by actuating the pen to release ink (step 92). This is repeated for each selected tissue section. Alternatively, when micrometers are manually controlled by the operator, the operator may move the x, y micrometers of the actuator 38 until controller 42 informs the operator via display 44 that the coordinates from position encoder 40 equals or approximately equals the x, y coordinate of a selected tissue section in the database. The operator then can actuate the pen to release ink and mark medium 36.

For manual marking of medium 36, step 90 is not needed and preferably medium 36 has grid lines 39 (FIG. 3B) to assist the operator in locating the x and y coordinates of each selected tissue section in reference to the zero reference mark 37 on medium 36.

Based on the x, y coordinates of each selected tissue section provided by controller 42 on display 44, the operator releases ink from a pen at the grid location corresponding to the x and y coordinates (step 92). For the z coordinate of each selected image, the operator may optionally use different color pens or ink densities to indicate the relative depth of the selected tissue section in the tissue.

After marking is completed, ring 32 is removed, but medium 36 is left in place on the surface 34a of the tissue via its adhesive layer. Thus, the marks on medium 36 identify on the tissue surface the sub-surface location of the part of tissue 34 presented in the selected tissue sections. Further, since the marks are macroscopic, i.e., can be viewed by the unaided eye, and images are microscopic, a single mark may represent the coordinates of multiple selected tissue sections in the database.

Referring to FIG. 5, a second embodiment of system 10 is shown in which all components are identical with FIG. 1, except the position encoder is removed, and the recording medium 36 has indicia which encode different locations without a zero reference mark. An example of the recording medium is shown as label 36c in FIG. 6. Label 36c is of a thin pliable transparent material, such as a piece of typical plastic wrap used in food storage. Label 36c has indicia 48 which is visible to microscope 11 when it is focused on label 36c. Indicia 48 encodes symbols which uniquely identify different locations on label 36c For example, indicia 48 may be a two-dimensional grid having lines which are each uniquely coded by symbols such as bar codes, letters, numbers, changes in frequency of dots or dashes in each line, or other types of encoding methods.

When label 36c is in focus, controller 42 is programmed to read from the image of label 36c the codes of indicia 48, and to decode them to identify the coordinates on label 36c represented by the codes. Coding and decoding may be performed using conventional techniques, such as optical character recognition or bar code reading.

The operation of system 10 in the embodiment of FIG. 5 is the same as in the first embodiment except in the manner the location information is obtained at step 86 of FIG. 4. Specifically, after the operator selects an imaged tissue section to be later marked, controller 42 or the operator moves the z axis micrometer of actuator 38 until indicia 48 on label 36c is in focus. Controller 42 then processes the image to read and decode the codes of the two intersecting lines of indicia 48 closest to the center of the image, or other coded symbol(s) closest to the center of the image. The decoded codes represent the coordinates of the selected tissue section, which are stored in the database in controller 42 as the location information for that selected tissue section. Next, the z axis micrometer is moved back to its home position where that micrometer was set when the tissue section was selected. This is repeated during surveying of the tissue to select tissue sections to be marked. After imaging is complete, the microscope is detached from actuator 38, and the operator reading indicia 48 then marks with a pen on label 36c the coordinates of each of the selected tissue sections. Controller 42 provides an output of these coordinates to the operator on display 44.

One advantage of this second embodiment is that label 36c may be pliable and flexible, thereby making it useful in circumstances when applied to a tissue having a surface with a curvature, such as the forehead or nose. Indicia 48 may stretch in different directions when applied to the tissue surface, such that the indicia may be non-linear.

FIG. 7 shows an optional television (video) camera 54 which may be used in the system 10 of FIG. 5 to read and decode indicia 48. A beam-splitter 50 may be located between plate 29 and lens 22 to reflect some of the light collected by lens 24 along a path 51 to camera 54 through focusing lens 52. Path 52 is coaxial with the optical axis of lens 24, and camera 54 is continuously focused on label 36c A display 56 receives signals from camera 54 and produces an image of the label 36c. Controller 42 may also receive the signals from camera 54. In operation, when each tissue section is selected by the operator, the two lines of indicia which intersect nearest the center in the image on display 56, or other coded symbol(s) nearest the center of the image, are read and decoded to provide the coordinates of the selected tissue section. Controller 42 using image signals from camera 54 may determine such coordinates similar to that described above for decoding indicia 48 imaged by microscope 11. Optionally, the operator may decode the coded indicia in the image on display 56, and record the coordinates as location information of the selected tissue section. The recorded location information is later used by the operator for manually produced marks of label 36c for each selected tissue section.

Referring to FIG. 8, a ring 58 is shown in a third embodiment of system 10 which is similar to the first embodiment ring 32. With ring 58, no recording medium 36 is required. Ring 58 has a template 60 with holes 62 extending through the template to the surface of tissue 34. For purposes of illustration, three holes 62 are shown, but a single hole or any number of holes may be used. When several holes are used, each hole has a unique shape, such as circle, triangle, and a cross. Aperture 30 is located in template 60, and an adhesive layer 64 on the bottom of template 60 bonds ring 58 to tissue 34.

In operation, ring 58 may be placed on tissue 34 without any recording medium 36 present, and reference marks are created directly on the surface of the tissue by the operator placing the tip of a pen with sterile ink in holes 62. Ring 58 is then moved by the operator, via actuator 38 (FIG. 1), to focus microscope 11 on each of the three reference mark formed in the three holes 62. When each of the reference marks is focused (and centered) on display 44, the operator directs controller 42 to set a reference location. The controller 42 in response reads position encoder 40, and stores the x, y, and z coordinates from the position encoder in a database in memory of controller 42. Thus, three reference locations are established on tissue surface 34a After surveying and selecting the coordinates of selected tissue sections, as in the first embodiment, the location on the tissue surface of the stored coordinates of the selected tissue sections is determined by controller 34 relative to their position from each of the reference marks for the subsequent operations for reviewing and printing marks. Marks may be printed on the surface of tissue 34 either automatically by a print head, similar to the first embodiment, or manually by an operator. Manually printing of the marks may be done after ring 58 is removed from tissue 34 by using the reference marks made on the surface of the tissue to locate the x and y coordinates for each selected tissue section. As in the first embodiment, the controller may provide the coordinates of each selected tissue section on the display 44, such coordinates may be displayed in terms of distances and angles from one or more reference marks in accordance with the distance of each x and y increment of position encoder 40. Holes 62 are uniquely shaped such that the reference marks created using each hole 62 can be identified after the ring 58 is removed from tissue 34.

Figure 9:
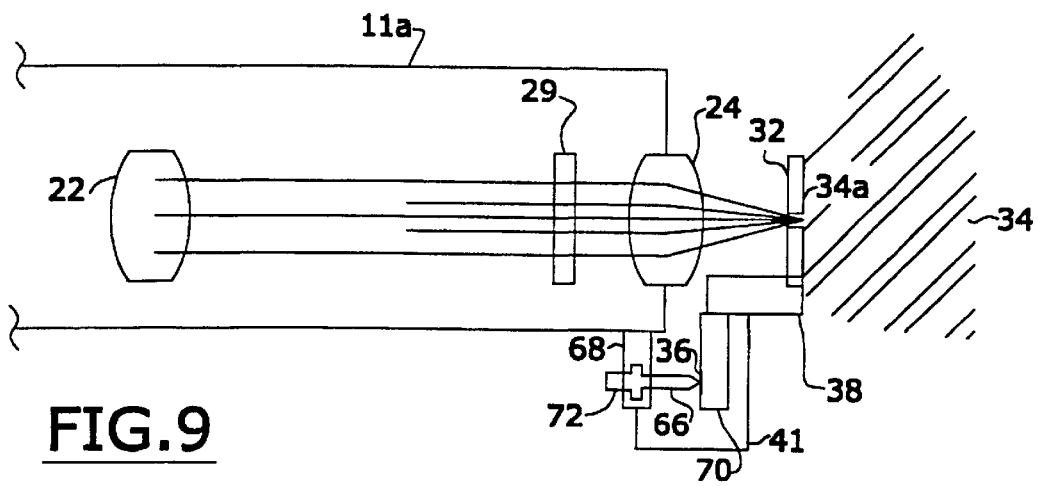
FIG. 9 is a block diagram of the part of the system of FIG. 5 shown within the dashed line 7—7 in accordance with a fourth embodiment of the system of the present invention which includes a pen coupled to the microscope for applying marks onto a recording medium.

Referring to FIG. 9, a fourth embodiment of system 10 is shown which is similar to the second embodiment, except that a pen 66 is connected by an arm 68 to microscope 11, via its projecting member 11a, and that recording medium 36 is set on a platen 70 which is connected to actuator 38 such that it moves with ring 32. Platen 70 is parallel to the plane defined by the x and y axes of actuator 38. Pen 66 is located over medium 36, and may be actuated by pen actuator 72 to apply ink onto medium 36. Medium 36 may be a thin non-elastic label, with or without a grid, and has an adhesive back layer for positioning the label onto platen 70. Coupler 41 is connected to arm 68 and actuator 38 such that actuator 38 moves ring 32 and platen 70 with respect to the optics of microscope 11.

The operation of the fourth embodiment of the system will now be described. Ring 32 is placed onto tissue 34 such that aperture 30 is over the part of tissue 34 to be imaged. Actuator 38, platen 70, and ring 32 may be a single assembly when ring 32 is positioned on tissue 34. A recording medium is placed under pen 66 on platen 70 and held in place by its adhesive back layer. Using microscope 11, the operator surveys below the surface of the tissue through imaged tissue sections on display 44. When the tissue section on display 44 is desired to be marked, the operator selects that section by using pen actuator 72 to apply ink from pen 66 onto medium 36 to generate a mark. This mark represents the position of the x and y micrometers of actuator 38 and the location information where the selected tissue section is with respect to surface 34a of tissue 34. The operator repeats surveying and selecting tissue sections in this manner to place multiple marks on medium 36, such as to outline the location of a lesion in the tissue. After imaging is completed, microscope 11 is detached from actuator 38. Medium 36 may be sized approximately equal to aperture 30 such that it may be peeled from platen 70 and placed on tissue surface 34a in aperture 30 utilizing the adhesive back layer of the medium.

Figure 10:
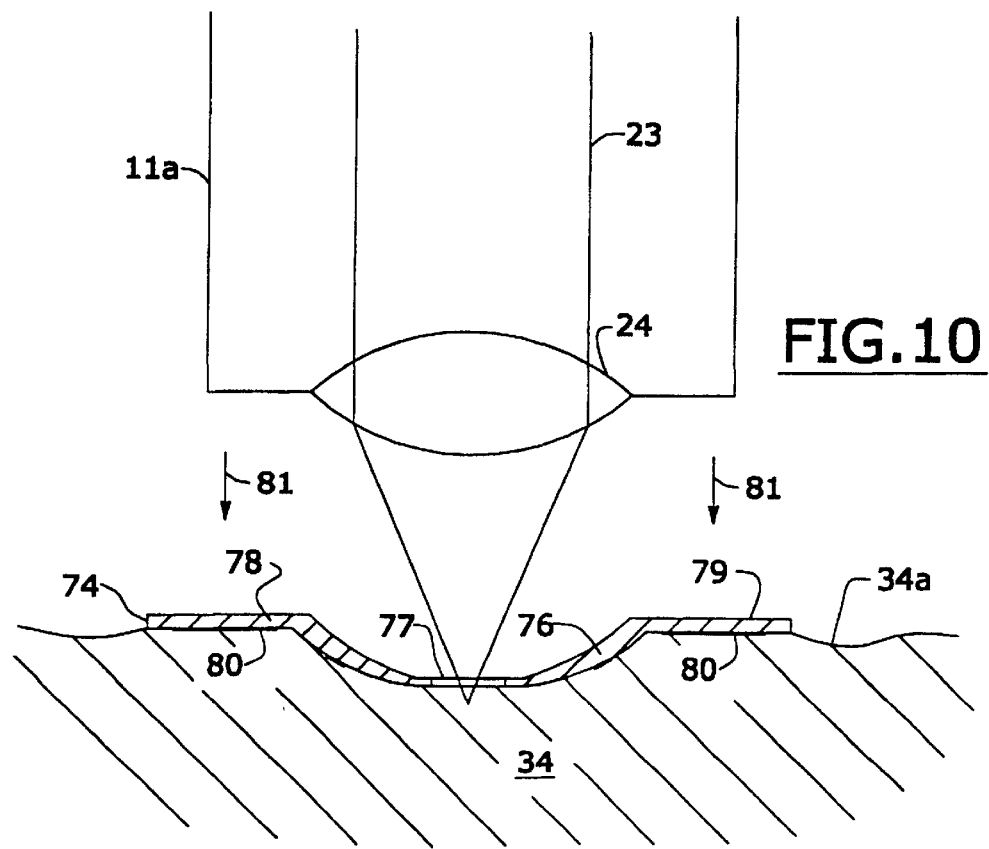
FIG. 10 is a side view of a further embodiment of a mechanism for tissue stabilization, which may be used in any of the four embodiments mentioned above, instead of the stabilization mechanism.

Referring to FIG. 10, a mechanism 74 is shown for stabilizing the tissue which may be used in system 10 in place of ring 32 or 58 in the above embodiments. Mechanism 74 has a convex region 76, and ends 78 and 79 extending from opposing sides of region 76. Mechanism 74 may be made of plastic or surgical steel, and region 76 has a window 77 made of a thin transparent material, such as plastic or glass. The bottom surface of ends 78 and 79 have an adhesive layer 80.

In operation, mechanism 74 is positioned on the tissue to be imaged, and the operator pushes down on the ends 78 and 79 of mechanism 74 in the direction of arrow 81. Adhesive layer 80 binds mechanism 74 to the surface 34a of tissue 34, such that convex region 76 is pressured against surface 34a. This automatically places the tissue 34 under convex region 76 under tension, thereby stabilizing such tissue to lens 24 via actuator 38 (not shown in FIG. 10). In addition to stabilizing tissue 34, convex region 76 localizes and planarizes the tissue 34 to lens 24 of microscope 11 Optionally, an index matching fluid may be placed on the surface of the tissue to be placed adjacent to convex region 76. If a recording medium is needed, an elastic recording medium, as described in the second embodiment, is placed on the tissue surface 34a prior to placement of mechanism 74 onto tissue 34.

From the foregoing description, it will be apparent that there has been provided an improved system for marking the locations of imaged tissue with respect to the surface of the tissue. Variations and modifications in the herein described system in accordance with the invention will undoubtedly suggest themselves to those skilled in the art. Accordingly, the foregoing description should be taken as illustrative and not in a limiting sense.

What is claimed is:

1. A system for marking on a recording medium the location of tissue sections imaged by a microscope with respect to the surface of the tissue in which the microscope has optics through which the microscope images the tissue, said system comprising:

means for stabilizing said tissue to said optics and localizing a portion of the surface of said tissue to said optics, wherein said stabilizing and localizing means is provided by a ring against the surface of the tissue, said ring having an aperture to localize the surface of the tissue to said optics;

means for selecting one or more tissue sections imaged by said microscope to be marked;

means for obtaining location information representing the location in the tissue of each said selected tissue section with respect to the surface of said tissue; and means for producing marks on a recording medium in accordance with said location information indicating the location with respect to said surface of the tissue of said selected tissue sections, wherein said recording medium is located upon the surface of said tissue when said location information is obtained and wherein said recording medium is located between the surface of the tissue and said aperture, said recording medium has indicia corresponding to different locations on said surface, and said means for obtaining location information further comprises means for determining said location information with respect to said indicia.

2. The system according to claim 1 further comprising means for moving said stabilizing and localizing means to adjust the position of said tissue with respect to said optics.

3. The system according to claim 1 wherein said microscope is a confocal microscope and said images are confocal images.

4. The system according to claim 1 wherein said microscope is operative in accordance with one of two-photon microscopy and optical coherence tomography.

5. The system according to claim 1 wherein said tissue represents one of naturally or surgically exposed tissue.

6. The system according to claim 1 wherein each of said marks on said recording medium are associated with one or more of said selected tissue sections.

7. The system according to claim 1 wherein at least one of the marks is of a color in accordance with the depth of the selected tissue section associated with the mark.

8. A system for marking on a recording medium the location of tissue sections imaged by a microscope with respect to the surface of the tissue in which the microscope has optics through which the microscope images the tissue, said system comprising:

means for stabilizing said tissue to said optics and localizing a portion of the surface of said tissue to said optics, wherein said stabilizing and localizing means is provided by a ring against the surface of the tissue, said ring having an aperture to localize the surface of the tissue to said optics;

means for selecting one or more tissue sections imaged by said microscope to be marked;

means for obtaining location information representing the location in the tissue of each said selected tissue section with respect to the surface of said tissue; and means for producing marks on a recording medium in accordance with said location information indicating the location with respect to said surface of the tissue of said selected tissue sections, wherein said recording medium is located upon the surface of said tissue when said location information is obtained and wherein said recording medium comprises a label applied to said surface of said tissue beneath said aperture of said ring.

9. The system according to claim 8 wherein said means for obtaining location information further comprises a means for determining an origin for referencing said location information with respect to said indicia.

10. The system according to claim 8 wherein said microscope is a confocal microscope and said images are confocal images.

11. The system according to claim 8 wherein said microscope is operative in accordance with one of two-photon microscopy and optical coherence tomography.

12. The system according to claim 8 wherein said tissue represents one of naturally or surgically exposed tissue.

13. The system according to claim 8 wherein each of said marks on said recording medium are associated with one or more of said selected tissue sections.

14. The system according to claim 8 wherein at least one of the marks is of a color in accordance with the depth of the selected tissue section associated with the mark.

15. A system for marking on a recording medium the location of tissue sections imaged by a microscope with respect to the surface of the tissue in which the microscope has optics through which the microscope images the tissue, said system comprising:
    means for stabilizing said tissue to said optics and localizing a portion of the surface of said tissue to said optics, wherein said stabilizing and localizing means is provided by a member adhesively coupled to the surface of the tissue having a convex region which planarizes said tissue and a window in said convex region through which said microscope images the tissue;
    means for selecting one or more tissue sections imaged by said microscope to be marked;
    means for obtaining location information representing the location in the tissue of each said selected tissue section with respect to the surface of said tissue; and
    means for producing marks on a recording medium in accordance with said location information indicating the location with respect to said surface of the tissue of said selected tissue sections, wherein said recording medium is located upon the surface of said tissue when said location information is obtained.

16. A method for marking on a recording medium the location of tissue sections imaged by a microscope with respect to the surface of the tissue in which the microscope has optics through which the microscope images the tissue, said method comprising the steps of:
    stabilizing said tissue to said optics of the microscope;
    selecting one or more tissue sections imaged by the microscope;
    determining location information representing the location in the tissue of each said selected tissue section with respect to the surface of said tissue; and
    producing marks on a recording medium in accordance with said location information indicating the location with respect to said surface of the tissue of said selected tissue sections, in which said recording medium is located upon said surface of said tissue when said determining step is carried out and wherein said recording medium comprises a label applied to the surface of the tissue through which said microscope images the tissue.

17. The method according to claim 16 wherein said selecting step futher comprises the step of moving one of said tissue and said microscope to provide to said optics different ones of said tissue sections.

18. The method according to claim 16 wherein said label has an adhesive layer attaching said label to the surface of the tissue.

19. The method according to claim 16 wherein said label is pliable.

20. The method according to claim 16 wherein said stabilizing step further comprises localizing through an aperture a portion of the tissue to said optics.

21. The method according to claim 16 wherein said recording medium has indicia and said determining step further comprises the step of determining an origin for referencing said location information with respect to said indicia.

22. The method according to claim 16 wherein said recording medium has indicia corresponding to different locations on said surface and said determining step further comprises the step of obtaining location information in accordance with said indicia.

23. The method according to claim 16 wherein said stabilizing step is carried out with the aid of a ring having an aperture through which said microscope images said tissue through said recording medium, in which said ring is attached to said microscope, and said ring is movable with respect to said microscope to enable said selecting step to select different ones of said imaged tissue sections.

24. The method according to claim 16 further comprising the step of imaging one or more tissue sections with the microscope in which said microscope is a confocal microscope.

25. The method according to claim 16 further comprising the step of imaging one or more tissue sections with the microscope in which said microscope is operative in accordance with one of two-photon microscopy and optical coherence tomography.

26. The method according to claim 16 wherein said tissue represents one of naturally or surgically exposure tissue.

27. The method according to claim 16 wherein said selected tissue sections have abnormalities associated with a lesion in the tissue.

28. A method for marking on a recording medium the location of tissue sections imaged by a microscope with respect to the surface of the tissue in which the microscope has optics through which the microscope images the tissue, said method comprising the steps of:
    stabilizing said tissue to said optics of the microscope, wherein said stabilizing step further comprises localizing through an aperture a portion of the tissue to said optics;
    selecting one or more tissue sections imaged by the microscope;
    determining location information representing the location in the tissue of each said selected tissue section with respect to the surface of said tissue; and
    producing marks on a recording medium in accordance with said location information indicating the location with respect to said surface of the tissue of said selected tissue sections, in which said recording medium is located upon said surface of said tissue when said determining step is carried out and wherein said recording medium is a thin plate situated between said aperture and said tissue surface.

29. The method according to claim 28 wherein said tissue represents one of naturally or surgically exposure tissue.

30. The method according to claim 28 wherein said selected tissue sections have abnormalities associated with a lesion in the tissue.

31. The method according to claim 28 wherein said recording medium has indicia and said determining step further comprises the step of determining an origin for referencing said location information with respect to said indicia.

32. The method according to claim 28 wherein said recording medium has indicia corresponding to different locations on said surface and said determining step further comprises the step of obtaining location information in accordance with said indicia.

33. The method according to claim 28 wherein said stabilizing step is carried out with the aid of a ring having said aperture through which said microscope images said tissue through said recording medium, in which said ring is attached to said microscope, and said ring is movable with respect to said microscope to enable said selecting step to select different ones of said imaged tissue sections.

34. The method according to claim 28 further comprising the step of imaging one or more tissue sections with the microscope in which said microscope is a confocal microscope.

35. The method according to claim 28 further comprising the step of imaging one or more tissue sections with the microscope in which said microscope is operative in accordance with one of two-photon microscopy and optical coherence tomography.

36. A method for marking on a recording medium the location of tissue sections imaged by a microscope with respect to the surface of the tissue in which the microscope has optics through which the microscope images the tissue, said method comprising the steps of:

stabilizing said tissue to said optics of the microscope;

selecting one or more tissue sections imaged by the microscope;

determining location information representing the location in the tissue of each said selected tissue section with respect to the surface of said tissue;

producing marks on a recording medium in accordance with said location information indicating the location with respect to said surface of the tissue of said selected tissue sections, wherein said recording medium is located on the surface of said tissue, said stabilizing step is carried out with the aid of a ring having an aperture through which said microscope images said tissue through said recording medium, in which said ring is attached to said microscope, and said ring is movable with respect to said microscope to enable said selecting step to select different ones of said imaged tissue sections, wherein said producing step further comprises the steps of detaching said microscope from said ring and applying marks on the recording medium with the aid of one of a print head and pen located in said aperture in accordance with said location information.

37. A method for marking on a recording medium the location of tissue sections imaged by a microscope with respect to the surface of the tissue in which the microscope has optics through which the microscope images the tissue, said method comprising the steps of:

stabilizing said tissue to said optics of the microscope;

selecting one or more tissue sections imaged by the microscope;

determining location information representing the location in the tissue of each said selected tissue section with respect to the surface of said tissue; and producing marks on a recording medium in accordance with said location information indicating the location with respect to said surface of the tissue of said selected tissue sections, wherein said recording medium is located on the surface of said tissue, said stabilizing step is carried out with the aid of a ring having an aperture through which said microscope images said tissue through said recording medium, in which said ring is attached to said microscope, and said ring is movable with respect to said microscope to enable said selecting step to select different ones of said imaged tissue sections, wherein said producing step further comprises the steps of detaching said microscope from said ring and manually applying marks on the recording medium in accordance with said location information.

38. A system for imaging tissue and for applying to a recording medium marks associated with the location of one or more images within the tissue, said system comprising:

a microscope for providing one or more sectional images of the tissue on a display;

a tissue stabilization ring applied to the surface of the tissue having an aperture through which said microscope images the tissue;

an actuator attachable to said microscope and said ring which is capable of moving one of said ring and microscope in three-dimensions to enable said microscope to image different sections of said tissue;

a controller having memory for enabling the selection of one or more of said images on said display;

a position encoder coupled to said actuator to provide signals to said controller representing the location in said tissue of the tissue sections imaged, in which the location of each of said selected images provided by the encoder is recorded in memory of said controller; and means operating in accordance with said controller for marking on said recording medium the recorded locations of the selected images with respect to the surface of the imaged tissue when said actuator is detached from said microscope, wherein said recording medium is located upon said tissue when said locations are recorded in memory of said controller and wherein said recording medium comprises a label applied to said surface of said tissue through which said microscope images the tissue through said aperture and wherein said means for marking comprises a print head having printing elements locatable in said aperture of said ring to apply marks to said recording medium at locations corresponding to at least one of the selected images with respect to the surface of the imaged tissue responsive to signals from said controller.

39. The system according to claim 38 wherein said print head is registered in said ring to align the printing elements with respect to two of said dimensions of movement of said actuator.

40. A system for imaging tissue and for applying to a recording medium marks associated with the location of one or more images within the tissue, said system comprising:

a microscope for providing one or more sectional images of the tissue on a display;

a tissue stabilization ring applied to the surface of the tissue having an aperture through which said microscope images the tissue;

an actuator attachable to said microscope and said ring which is capable of moving one of said ring and microscope in three-dimensions to enable said microscope to image different sections of said tissue;

a controller having memory for enabling the selection of one or more of said images on said display;

a position encoder coupled to said actuator to provide signals to said controller representing the location in said tissue of the tissue sections imaged, in which the location of each of said selected images provided by the encoder is recorded in memory of said controller; and means operating responsive to signals from said controller for enabling marking on said recording medium the recorded locations of the selected images with respect to the surface of the imaged tissue when said actuator is detached from said microscope, wherein said recording medium is located upon said tissue when said locations are recorded in memory of said controller, and wherein said recording medium comprises a label applied to said surface of said tissue through which said microscope images the tissue through said aperture and wherein said means comprises inking means coupled to said actuator adjacent said aperture for moving said inking means and applying ink at one or more locations to said recording medium corresponding to at least one of the selected images with respect to the surface of the imaged tissue.

41. The system according to claim 40 wherein said inking means represents a pen operating responsive to said controller to apply ink.

42. The system according to claim 40 wherein said inking means represents a pen actuated manually to apply ink to said recording medium.

43. The system according to claim 40 wherein said inking means moves responsive to manually movement of said actuator to recorded locations as provided by said controller.

44. The system according to claim 40 wherein said inking means moves responsive to manually movement of said actuator to recorded locations in accordance with signals from said controller.

45. The system according to claim 40 wherein said means is enabled by manually actuating ink from a pen locatable in said aperture of said ring to apply marks to said recording medium at locations corresponding to at least one of the selected images with respect to the surface of the imaged tissue responsive to information provided on said display from said controller in accordance with said recorded locations.

46. The system according to claim 40 wherein said controller provides an origin location for said encoder and said recorded locations are referenced by said origin location.

47. The system according to claim 46 wherein said origin location is in accordance with a reference identifier on the recording medium imaged by said microscope on said display.

48. The system according to claim 40 wherein said controller is part of said microscope.

49. A system for imaging tissue and for applying to a recording medium marks associated with the location of one or more images within the tissue, said system comprising:

a microscope for providing one or more sectional images of the tissue on a display;

a tissue stabilization ring applied to the surface of the tissue having an aperture through which said microscope images the tissue;

an actuator attachable to said microscope and said ring which is capable of moving one of said ring and microscope in three-dimensions to enable said microscope to image different sections of said tissue;

a controller having memory for enabling the selection of one or more of said images on said display;

a position encoder coupled to said actuator to provide signals to said controller representing the location in said tissue of the tissue sections imaged, in which the location of each of said selected images provided by the encoder is recorded in memory of said controller; and means operating in accordance with said controller for enabling marking on said recording medium the recorded locations of the selected images with respect to the surface of the imaged tissue when said actuator is detached from said microscope, wherein said recording medium is located upon said tissue when said locations are recorded in memory of said controller and wherein said recording medium comprises a label applied to said surface of said tissue beneath said aperture of said ring, and said ring is removable from said surface of said tissue.

50. A system for imaging tissue and for applying to a recording medium marks associated with the location of one or more images within the tissue, said system comprising:

a microscope for providing one or more sectional images of the tissue on a display;

a tissue stabilization ring applied to the surface of the tissue having an aperture through which said microscope images the tissue;

an actuator attachable to said microscope and said ring which is capable of moving one of said ring and microscope in three-dimensions to enable said microscope to image different sections of said tissue;

a controller having memory for enabling the selection of one or more of said images on said display;

a position encoder coupled to said actuator to provide signals to said controller representing the location in said tissue of the tissue sections imaged, in which the location of each of said selected images provided by the encoder is recorded in memory of said controller; and means operating in accordance with said controller for enabling marking on said recording medium the recorded locations of the selected images with respect to the surface of the imaged tissue when said actuator is detached from said microscope, wherein said recording medium is the surface of said tissue, said ring has a template for one or more reference identifiers through which ink is applied to the surface of said tissue, and each of said reference identifiers are imaged by said microscope on said display and their encoder position stored in memory of the controller as reference locations by which said recorded locations are referenced.

51. A system for imaging tissue and for applying to a recording medium marks associated with the location of one or more images within the tissue, said system comprising:

a microscope for providing one or more sectional images of the tissue on a display;

a tissue stabilization ring applied to the surface of the tissue having an aperture through which said microscope images the tissue;

an actuator attachable to said microscope and said ring which is capable of moving one of said ring and microscope in three-dimensions to enable said microscope to image different sections of said tissue;

a controller having memory and coupled to said display in which said controller enables the selection of one or more of said images on said display;

a recording medium on the surface of said tissue through which said microscope images through said aperture, the recording medium having indicia uniquely identifying different locations on said recording medium;

said controller having means for determining the location of each of said selected images from said indicia when said indicia associated with each of said selected images is focused by said microscope, and storing the determined location of each of said selected images in memory of said controller; and means operating in accordance with said controller for enabling marking on said recording medium the recorded locations of the selected images with respect to the surface of the imaged tissue when said actuator is detached from said microscope.

52. The system according to claim 51 wherein said recording medium is pliable.

53. A system for imaging tissue and for applying to a recording medium marks associated with the location of one or more images within the tissue, said system comprising:

a microscope having optics for providing one or more sectional images of tissue on a display;

a tissue stabilization ring applied to the surface of the tissue having an aperture through which said microscope images the tissue;

an actuator attachable to said microscope and said ring which is capable of moving one of said ring and microscope in three-dimensions to enable said microscope to image different sections of said tissue;

a recording medium on the surface of said tissue through which said microscope images through said aperture having indicia uniquely identifying different locations on said recording medium;

a controller having memory and for enabling the selection of one or more of said images on said display;

a camera coupled to said controller focused on said recording medium through said optics of said microscope;

said controller having means for determining the location of each of said selected images from imaged indicia on said recording medium provided by said camera, and storing the determined location of each of said selected images in memory of said controller; and means operating in accordance with said controller for enabling marking on said recording medium the recorded locations of the selected images with respect to the surface of the imaged tissue when said actuator is detached from said microscope.

54. A system for imaging tissue and for applying to a recording medium marks associated with the location of one or more images within the tissue, said system comprising:

a microscope for providing one or more sectional images of the tissue on a display;

a tissue stabilization member adhesively coupled to the surface of the tissue having a convex region which planarizes said tissue and a window in said convex region through which said microscope images the tissue;

an actuator attachable to said microscope and said ring capable of moving one of said ring and microscope in three-dimensions to enable said microscope to image different sections of said tissue;

a controller having memory for enabling the selection of one or more of said images on said display;

a position encoder coupled to said actuator to provide signals to said controller representing the location in said tissue of the tissue sections imaged, in which the location of each of said selected images provided by the encoder is recorded in memory of said controller; and means operating in accordance with said controller for enabling marking on said recording medium the recorded locations of the selected images with respect to the surface of the imaged tissue when said actuator is detached from said microscope.

55. The system according to claim 54 wherein said recording medium is one of said surface of said tissue and a label applied to said surface of said tissue beneath said window.

56. A system for a correlating the location of tissue sections imaged by a microscope with respect to the surface of the tissue in which the microscope has optics through which the microscope images sections of the tissue, said system comprising:

means for stabilizing said tissue to said optics and localizing the surface of said tissue to said optics;

means for selecting one or more images presenting tissue sections which contain distinguishable tissue;

means for obtaining location information representing the location in the tissue of each of said selected images with respect to the surface of said tissue; and a recording member on the surface of said tissue through which said microscope images said tissue when said location information is obtained; and means for applying marks to automatically print said marks in accordance with said obtained location information.

57. A system for correlating the location of tissue sections imaged by a microscope with respect to the surface of the tissue in which the microscope has optics through which the microscope images sections of the tissue, said system comprising:

means for stabilizing said tissue to said optics and localizing the surface of said tissue to said optics;

means for selecting one or more images presenting tissue sections which contain distinguishable tissue;

means for obtaining location information representing the location in the tissue of each of said selected images with respect to the surface of said tissue;

a recording member on the surface of said tissue through which said microscope images said tissue when said location information is obtained; and wherein said means for obtaining location information utilizes imaging means to read indicia on said recording member identifying different locations on the recording member.

58. The system according to claim 57 further comprising means for applying marks on said recording member under manual assistance in accordance with said obtained location information.

* * * * *